United States Patent
Hudnall et al.

(10) Patent No.: US 6,271,424 B1
(45) Date of Patent: Aug. 7, 2001

(54) PROCESS FOR THE PURIFICATION OF MONOTERTIARYBUTYL HYDROQUINONE

(75) Inventors: Phillip Montgomery Hudnall, Kingsport; Lucian Boldea, Jonesborough, both of TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 09/608,211

(22) Filed: Jun. 30, 2000

Related U.S. Application Data

(60) Provisional application No. 60/212,164, filed on Jun. 16, 2000.

(51) Int. Cl.$^7$ .................................................. C07C 37/68
(52) U.S. Cl. ............................................................ 568/753
(58) Field of Search ............................................. 568/753

(56) References Cited

U.S. PATENT DOCUMENTS

| | | |
|---|---|---|
| 2,722,556 | 11/1955 | Young et al. . |
| 3,982,944 | 9/1976 | Ohi et al. . |
| 4,323,713 | 4/1982 | Engel . |
| 4,323,715 | 4/1982 | Engel et al. . |
| 5,087,771 | 2/1992 | Hilderbrand . |

FOREIGN PATENT DOCUMENTS

| | | |
|---|---|---|
| 62-81339A | 4/1987 | (JP) . |
| 62-81340A | 4/1987 | (JP) . |
| 32-36340A | 10/1991 | (JP) . |

*Primary Examiner*—Michael L. Shippen
(74) *Attorney, Agent, or Firm*—Cheryl J. Tubach; Bernard J. Graves, Jr.

(57) ABSTRACT

The present invention relates to a method of making purified monotertiarybutyl hydroquinone containing less than 0.2% (wt.) of 2,5 ditertiarybutyl hydroquinone. This method includes heating a composition of monotertiarybutyl hydroquinone and 2,5 ditertiarybutyl hydroquinone in a solvent mixture of a polar solvent and a non-polar solvent. During this step, the non-polar solvent is substantially stripped-off and at least part of the 2,5 ditertiarybutyl hydroquinone is solidified, which is separated from the non-solidified composition. The remaining non-solidified composition and polar solvent are mixed with a non-polar solvent of the same type as was previously stripped-off. The polar solvent, which contains the purified monotertiarybutyl hydroquinone, is separated from the non-polar solvent. This purified monotertiarybutyl hydroquinone is separated the from the polar solvent to produce purified monotertiarybutyl hydroquinone containing less than 0.2% (wt.) of 2,5 ditertiarybutyl hydroquinone.

23 Claims, 1 Drawing Sheet

US 6,271,424 B1

PROCESS FOR THE PURIFICATION OF MONOTERTIARYBUTYL HYDROQUINONE

CROSS REFERENCE TO RELATED APPLICATION

This application claims priority to U.S. Provisional Application entitled "Process for the Purification of Monotertiarybutyl Hydroquinone," filed Jun. 16, 2000, Ser. No. 60/212,164, (and listed inventors Phillip M. Hudnall and Lucian Boldea), which is incorporated by reference in its entirety for all purposes.

FIELD OF THE INVENTION

The present invention relates to the purification of monotertiarybutyl hydroquinone. More particularly the present invention relates to an improved process for producing food-grade tertiarybutyl hydroquinone.

BACKGROUND OF THE INVENTION

Food-grade tertiarybutyl hydroquinone ("TBHQ") is useful as a flavor and aroma preservative. Food-grade TBHQ is required by the Food Chemicals Codex Specifications to have at least 99.0% (wt) monotertiarybutyl hydroquinone ("MTBHQ") on a dry basis and less than 0.2% (wt.) of the major impurity, 2,5-ditertiarybutyl hydroquinone ("DTBHQ"). Additional Food Chemicals Codex Specifications for TBHQ are as follows: 0.2% (wt.) maximum t-butyl-p-benzoquinone, 10 ppm maximum heavy metals, melting range between 126.5° C. and 128.5° C., 0.1% (wt.) maximum hydroquinone, 0.0025% (wt.) maximum toluene, and an ultraviolet absorbance for polynuclear hydrocarbons with maximum absorbances at four different wavelength regions. As a result of such low impurity requirements, the production of relatively pure MTBHQ is essential to the production of food-grade TBHQ.

MTBHQ production is well known in the art. For example, U.S. Pat. No. 2,722,556 to Young, et al., the disclosure of which is incorporated herein by reference in its entirety, discloses a process for producing MTBHQ by reacting hydroquinone with isobutylene or tertiarybutyl alcohol. The crude MTBHQ produced by this process does not meet the TBHQ Food Chemicals Codex Specifications because of high impurity levels. The main impurity in the crude MTBHQ, DTBHQ, is produced in large quantities during the butylation of hydroquinone reaction.

One method of purifying MTBHQ is discussed in the background section of U.S. Pat. No. 5,087,771 to Hilderbrand. This reference discloses purification of crude MTBHQ by dissolving crude, water-wet MTBHQ crystals in toluene, decanting the water, and filtering the hot solution to a crystallizer. The majority of the DTBHQ remains in the toluene mother liquor as the MTBHQ crystallizes. This process is expensive and is very intensive in both labor and equipment, requiring long batch cycle times and specialized equipment.

An alternative method of purifying MTBHQ is taught in U.S. Pat. No. 5,087,771 to Hilderbrand. In this method, crude, water-wet MTBHQ crystals are contacted with a non-polar solvent, such as naphtha, at an elevated temperature. The MTBHQ crystals form a slurry mixture with the non-polar solvent. The temperature of the mixture is lowered and TBHQ is obtained as a solid from the solvent at a temperature above the crystallization point of DTBHQ. The preliminary isolation step required in this process to obtain the crude MTBHQ crystals results in relatively high processing costs, added processing time and extra equipment usage.

JP 62081339 to Hasegawa et al. also describes the purification of crude MTBHQ. In this process, crude, water-wet MTBHQ crystals are purified by forming an extractable eutectic mixture and subsequent solid-liquid extraction. The eutectic mixture is made possible by the unique properties of MTBHQ and DTBHQ: the melting point of a mixture of MTBHQ and DTBHQ is lower than either the melting point of MTBHQ (126° C.) or DTBHQ (216° C.). Although effective, this method requires careful control of temperature, time and flow rate in addition to the high processing costs due to the required preliminary isolation of crude MTBHQ crystals.

In spite of the foregoing, the need still exists for a cost-effective process to produce purified MTBHQ, particularly for removing DTBHQ, such as an in-process purification of MTBHQ.

SUMMARY OF THE INVENTION

The present invention relates to a method of making purified monotertiarybutyl hydroquinone comprised of less than 0.2% (wt.) of 2,5 ditertiarybutyl hydroquinone, wherein the method comprises: a) heating a first composition in a solvent mixture, wherein the first composition comprises monotertiarybutyl hydroquinone and 2,5 ditertiarybutyl hydroquinone and the solvent mixture comprises a polar solvent and a non-polar solvent to substantially strip-off the non-polar solvent; b) solidifying at least part of the 2,5 ditertiarybutyl hydroquinone; c) separating the solidified 2,5 ditertiarybutyl hydroquinone from the non-solidified first composition to form a second composition comprised of the non-solidified first composition and the polar solvent; d) mixing the second composition with a non-polar solvent of the same type as the nonpolar solvent of step (a); e) separating the polar solvent from the non-polar solvent, wherein the polar solvent contains the purified monotertiarybutyl hydroquinone; and f) separating the purified monotertiarybutyl hydroquinone from the polar solvent to produce purified monotertiarybutyl hydroquinone comprised of less than 0.2% (wt.) of 2,5 ditertiarybutyl hydroquinone.

The present invention also relates to a method of making purified monotertiarybutyl hydroquinone comprised of less than 0.2% (wt.) of 2,5 ditertiarybutyl hydroquinone, wherein the method comprises: a) heating a composition in a solvent mixture wherein: (i) the composition comprises monotertiarybutyl hydroquinone and 2,5 ditertiarybutyl hydroquinone, (ii) the solvent mixture comprises a polar solvent and a non-polar solvent, and (iii) the composition and solvent mixture are heated to a temperature at or above the melting point of the composition; b) separating the polar solvent from the solvent mixture at a temperature at or above the melting point of the composition, wherein the polar solvent contains the purified monotertiarybutyl hydroquinone; and c) separating the purified monotertiarybutyl hydroquinone from the polar solvent to produce purified monotertiarybutyl hydroquinone comprised of less than 0.2% (wt.) of 2,5 ditertiarybutyl hydroquinone.

The present invention is further directed to a method of making purified monotertiarybutyl hydroquinone comprised of less than 0.2% (wt.) of 2,5 ditertiarybutyl hydroquinone, wherein the method comprises: a) heating a composition in a solvent mixture wherein the composition comprises monotertiarybutyl hydroquinone and 2,5 ditertiarybutyl hydroquinone, and the solvent mixture comprises a polar solvent and a non-polar solvent, b) separating the polar solvent from the solvent mixture in a liquid-liquid extraction, wherein the polar solvent contains the purified monotertiarybutyl hydroquinone; and c) separating the purified monotertiarybutyl hydroquinone from the polar solvent to produce purified monotertiarybutyl hydroquinone comprised of less than 0.2% (wt.) of 2,5 ditertiarybutyl hydroquinone.

Advantages of the invention will be obvious from the description, or may be learned by practice of the invention. Additional advantages of the invention will be realized and attained by means of the elements and combinations particularly pointed out in the appended claims. It is to be understood that both the foregoing general description and the following detailed description are exemplary and explanatory of preferred embodiments of the invention, and are not restrictive of the invention, as claimed.

DETAILED DESCRIPTION OF THE INVENTION

Figure 1:
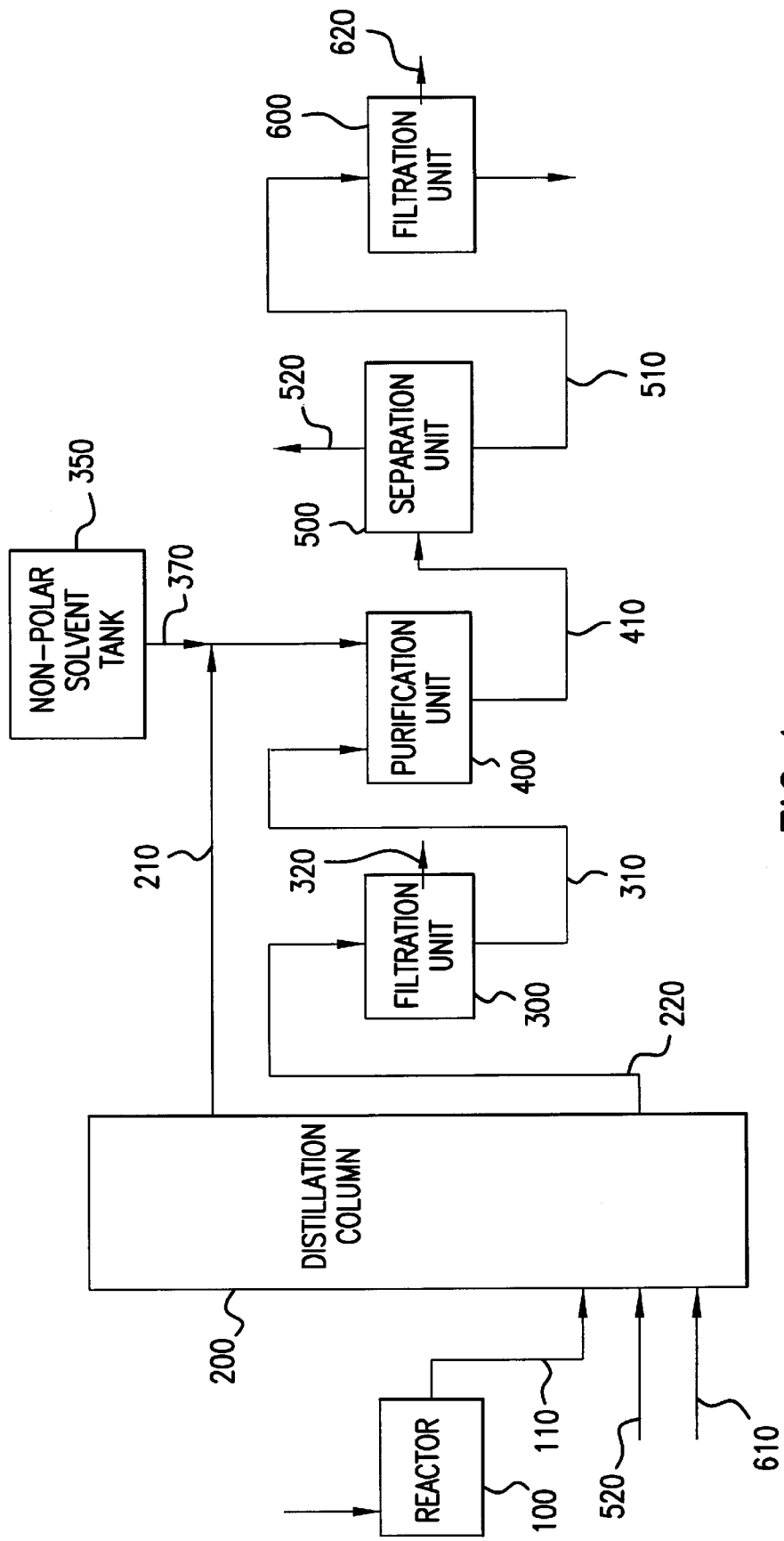
FIG. 1 is a process diagram of a preferred embodiment of the invention.

The present invention may be understood more readily by reference to the following detailed description of the inventions, including the examples provided herein and the FIGURE. It is to be understood that this invention is not limited to the specific processes and conditions described, as specific processes and/or process conditions for purifying MTBHQ as such may, of course, vary. It is also to be understood that the terminology used herein is for the purpose of describing particular embodiments only and is not intended to be limiting.

It must also be noted that, as used in the specification and the appended claims, the singular forms "a," "an" and "the" comprise plural referents unless the context clearly dictates otherwise. For example, reference to processing or using a "composition" or "solvent" from the process of this invention is intended to comprise the processing of a plurality of compositions or solvents, potentially in a plurality of discrete processing steps.

Ranges may be expressed herein as from "about" or "approximately" one particular value and/or to "about" or "approximately" another particular value. When such a range is expressed, another embodiment comprises from the one particular value and/or to the other particular value. Similarly, when values are expressed as approximations, by use of the antecedent "about," it will be understood that the particular value forms another embodiment.

As used herein, DTBHQ means 2,5-ditertiarybutyl hydroquinone, MTBHQ means monotertiarybutyl hydroquinone, and TBHQ means food-grade tertiarybutyl hydroquinone. No purity levels are implicated by the above except that TBHQ meets all Food Chemicals Codex Specifications.

The present invention relates to, in a first major embodiment, a method of making purified MTBHQ containing less than 0.2% (wt.) of DTBHQ (relative to the total MTBHQ). This method includes heating a composition of MTBHQ and DTBHQ in a solvent mixture of a polar solvent and a non-polar solvent. The non-polar solvent is substantially stripped-off and at least part of the DTBHQ is solidified, which is separated from the non-solidified composition. The remaining non-solidified composition and polar solvent are mixed with a non-polar solvent of the same type as was previously stripped-off. The polar solvent, which contains the purified MTBHQ, is separated from the non-polar solvent. This purified MTBHQ is separated the from the polar solvent to produce purified MTBHQ containing less than 0.2% (wt.) of DTBHQ (relative to the total MTBHQ).

Moreover, the present invention relates to, in a second major embodiment, a method of making purified MTBHQ containing less than 0.2% (wt.) of DTBHQ (relative to the total MTBHQ), wherein the method includes heating a composition containing MTBHQ and DTBHQ in a solvent mixture containing a polar solvent and a non-polar solvent to a temperature at or above the melting point of the composition. The polar solvent, which contains the purified MTBHQ, is separated from the solvent mixture at a temperature at or above the melting point of the composition. The purified MTBHQ is separated from the polar solvent to produce purified MTBHQ comprised of less than 0.2% (wt.) of DTBHQ (relative to the total MTBHQ).

The present invention is further directed to, in a third major embodiment, a method of making purified MTBHQ containing less than 0.2% (wt.) of DTBHQ, wherein the method includes heating a composition containing MTBHQ and DTBHQ in a solvent mixture containing a polar solvent and non-polar solvent. The polar solvent, which contains the purified MTBHQ, is separated from the solvent mixture in a liquid-liquid extraction. The purified MTBHQ is separated from the polar solvent to produce purified MTBHQ comprised of less than 0.2% (wt.) of DTBHQ.

The composition of the second and third major embodiments is analogous to the non-solidified composition of the first major embodiment. Therefore, the composition referenced in the second and third major embodiments has the same meaning as the non-solidified composition hereinafter described. All other terms have the same meaning for all three major embodiments.

The composition of MTBHQ and DTBHQ is preferably prepared by the process disclosed in U.S. Pat. No. 2,722,556 to Young, et al. This process entails reacting hydroquinone with either isobutylene or tertiarybutyl alcohol in the presence of a strong acid catalyst. Therefore, the composition of MTBHQ and DTBHQ may include other materials such as hydroquinone, isobutylene, tertiarybutyl alcohol, an acid catalyst, water, non-polar solvent, t-butyl-p-benzoquinone, and/or heavy metals.

The non-polar solvent of the solvent mixture can be aromatic or non-aromatic. In one embodiment, the non-polar solvent is chosen to bring the boiling point of the solvent mixture to between about 85° C. and about 115° C. at atmospheric pressure when the nonpolar solvent is stripped-off. Suitable non-polar solvents include, but are not limited to, toluene, xylene, n-heptane, octane, isooctane, cyclohexane, and naphtha. In one preferred embodiment, the non-polar solvent is naphtha. In another preferred embodiment, the nonpolar solvent is toluene or xylene.

The polar solvent of the solvent mixture is used to lower the boiling point of the solvent mixture. As such, any polar solvent which is immissable with the non-polar solvent may be used. Preferably, the polar solvent is water.

The proportion of polar solvent to non-polar solvent in the solvent mixture is only important in as much as it affects the boiling point of the solvent mixture. As such, the stripping-off of the non-polar solvent changes the proportion of solvents to maintain approximately the same boiling point. In one preferred embodiment, the proportion of polar solvent to non-polar solvent results in a solvent mixture boiling point between about 85° C. and about 115° C. at atmospheric pressure. In another preferred embodiment, this proportion results in a solvent mixture boiling point between about 90° C. and about 100° C. at atmospheric pressure.

The non-polar solvent is stripped-off in any equipment that allows for pressure and temperature control. If the solvents or proportions are chosen such that the boiling point is less than 85° C. at atmospheric pressure, the pressure must be increased to compensate. In one preferred embodiment utilizing toluene, the non-polar solvent (toluene) is stripped-off in a stripper or distillation column at atmospheric pressure.

The amount of time that the composition of MTBHQ and DTBHQ remains in contact with the solvent mixture while the non-polar solvent is stripped-off does not affect the invention. In one preferred embodiment, the contact time is sufficient to allow the non-polar solvent to be substantially stripped-off.

As the non-polar solvent is stripped-off, at least some of the DTBHQ solidifies. The solidified DTBHQ may be separated from the non-solidified composition and the remaining solvent mixture by any method known in the art. In one preferred embodiment, the solidified DTBHQ is separated by filtration and/or centrifugation.

The remaining non-solidified composition and polar solvent are then mixed in a purification vessel with a non-polar solvent of the same type as the non-polar solvent that was previously stripped-off. The polar solvent may contain some non-polar solvent that was not previously stripped-off. In a preferred embodiment, the previously stripped-off non-polar solvent is reused in this step and mixed with the non-solidified composition and solvent mixture. In another preferred embodiment, this reused nonpolar solvent is toluene.

The amount of the non-polar solvent used is a function of the respective partition coefficients of the MTBHQ and DTBHQ in the two solvent system. The amount of nonpolar solvent in most cases must be minimized to reduce the loss of MTBHQ to the nonpolar solvent. This amount of non-polar solvent is preferably between about 1 and 10 weight percent based on the total weight of the polar and non-polar solvents.

The non-solidified composition may contain, in addition to MTBHQ, DTBHQ, water, non-polar solvent, t-butyl-p-benzoquinone, hydroquinone, isobutylene, tertiarybutyl alcohol, and/or the acid catalyst. In one preferred embodiment, the non-solidified composition contains between about 95% (wt.) and about 99% (wt.) MTBHQ on a dry basis of the non-solidified composition.

The non-solidified composition may also be mixed with any water soluble reducing agent known in the art, such as ascorbic acid, erythorbic acid, sodium hydrosulfite, sodium erythorbate, sodium metabisulfite, or sulfur dioxide. In a preferred embodiment, the water soluble reducing agents are ascorbic acid and/or sodium bisulfate, since these would not necessitate expensive corrosion resistant equipment.

The amount of water soluble reducing agent used in the process of the present invention is generally between about 0.1% (wt.) and about 0.5% (wt.) based on a dry basis of the total composition. The amount of reducing agent used in the process of the present invention is preferably from about 0.15% (wt.) to 0.4% (wt.), with 0.2% (wt.) being most preferred.

In one preferred embodiment, the mixing of the non-solidified composition and polar solvent with the non-polar solvent and optionally with a water soluble reducing agent, occurs before or during heating these components. Preferably, the mixing occurs near the boiling point of the most volatile component in the mixture (in most cases the azeotrope of the two solvents). In yet another preferred embodiment, the boiling point will be between about 85° C. to about 150° C. at a pressure of about 15 psig to about 45 psig. If a solvent is chosen that boils lower than the desired purification temperature, then the pressure in the purification vessel must be increased to compensate. The high pressure mode of operation offers the advantage of increased throughput due to higher concentrations in the feed to the extractor system.

In another preferred embodiment, this mixing substantially occurs approximately at or above the melting point temperature of the non-solidified composition. Suitable temperatures range from about 80° C. to about 118° C., with temperatures in the range of about 85° C. to about 105° C. being most preferable.

The amount of time of heating and/or mixing is not critical to the present invention. In one preferred embodiment, the heating and/or mixing occurs for at least 5 minutes. In another preferred embodiment, this heating and/or mixing occurs from about 5 minutes to about 60 minutes.

The polar and non-polar solvents are then ultimately separated. In one preferred embodiment, this separation occurs by any method known in the art while keeping the temperature at or above the melting point temperature of the non-solidified composition. In another preferred embodiment, this separation occurs by liquid-liquid extraction.

The heating and/or mixing of the non-solidified composition with a non-polar solvent and/or separation of the non-polar solvent from the polar solvent may occur in any equipment that is compatible with the process conditions. Suitable equipment includes a rotating disc column, Scheibel column, vertically agitated extractor, fixed bed extractor, high pressure extractor, vertical mixer-settler, horizontal mixer-settler, and/or one or more vessel liquid-liquid extractors.

After separation of the solvents, the polar solvent may contain some non-polar solvent, preferably no more than 10% (wt.). The polar solvent also contains a substantial portion of the purified MTBHQ. However, the non-polar solvent may also contain some MTBHQ and some polar solvent. As such, to increase the overall yield, the non-polar solvent may be recycled to the stripper or distillation column to form at least part of the initial solvent mixture in future purifications. Trace levels of non-polar solvent may be removed from the polar solvent by an additional stripping operation.

The separated polar solvent may be cooled to allow the purified MTBHQ to solidify. The crystallization can be carried out at low temperatures to minimize product loss to the filtrate. In one preferred embodiment, the polar solvent is cooled to at least 25° C., more preferably to at least 15° C.

After the purified MTBHQ solidifies, the polar solvent is separated from the purified MTBHQ. The polar solvent may then be recycled to the stripper or distillation column to form at least part of the initial solvent mixture in future purifications. This separation step may be performed in any suitable equipment for solid-liquid separation, including filtration and centrifugation devices.

The process according to the present invention may include a washing step after the separation step in which the MTBHQ is washed with a polar solvent. The polar solvent is preferably the same polar solvent as that which was separated from the purified MTBHQ. Most preferably, the polar solvent is water.

The process of the present invention may also entail a drying step at the end of the process. This drying step is preferably conducted under vacuum at a temperature between about 50° C. and 90° C. with about 65° C. and a vacuum of 25" Hg being most preferred. The resulting purified MTBHQ contains less than approximately 0.2% (wt.) of DTBHQ (relative to the total MTBHQ). In one preferred embodiment, the purified MTBHQ meets all Food Chemicals Codes Specifications and is suitable for use as TBHQ.

Without limitation as to the theory of the process, the purification process of the present invention utilizes the differences in partition coefficients between MTBHQ and DTBHQ. For example, MTBHQ has a partition coefficient of about 10 and DTBHQ has a partition coefficient of about 300 between toluene and water. Therefore, DTBHQ has a greater affinity for toluene than MTBHQ's affinity for toluene so more DTBHQ than MTBHQ will be present in the toluene layer in a solvent mixture. Consequently, removal of DTBHQ thereby purifying MTBHQ occurs during separations of the polar solvent from the non-polar solvent, even with liquid-liquid type separations.

Referring now to FIG. 1, which is one preferred embodiment of the present invention, the present invention provides a method of making purified MTBHQ wherein the reaction between hydroquinone and either isobutylene or tertiarybutyl alcohol in the presence of a strong acid catalyst occurs in a first reactor 100 to produce crude MTBHQ. The reaction proceeds in a solvent mixture of a non-polar solvent and a polar solvent. The majority of the crude MTBHQ is in the non-polar solvent. As such, the non-polar solvent containing crude MTBHQ is transferred 110 to a distillation column 200.

In the distillation column 200, at least part of the non-polar solvent is stripped-off and replaced with a polar solvent. In the embodiment depicted in FIG. 1, a portion of the stripped-off non-polar solvent is transferred 210 to a purification vessel 400. The remaining solvent mixture, which includes crude MTBHQ and DTBHQ in solution in the polar solvent ("the non-solidified composition") and solidified DTBHQ, is transferred 220 along to the filtration unit 300.

The filtration unit 300 separates the solidified DTBHQ from the non-solidified composition and solvent mixture. The non-solidified composition and solvent mixture are then transferred 310 to the purification vessel 400, and the solidified DTBHQ is collected 320.

In the purification vessel 400, the transferred non-solidified composition and solvent mixture 310 are contacted with a portion of the transferred non-polar solvent 210 from the distillation column 200. Such contact may include heating and/or mixing in the purification vessel 400. In one preferred embodiment, the mixing substantially occurs at or above the melting point temperature of the non-solidified composition. Following this heating and/or mixing, the contents of the purification vessel 400 are transferred 410 to a separation vessel 500.

In one preferred embodiment, the separation vessel 500 allows a substantially liquid-liquid extraction. The non-polar solvent is substantially separated from the polar solvent in the separation vessel 500. The separated non-polar solvent is recycled 520 back to the distillation column 200. The separated polar solvent, which contains the purified MTBHQ, is transferred 510 to the filtration vessel 600.

It is to be understood that the contact between the non-polar solvent and the non-solidified composition and solvent mixture and the separation of the purified MTBHQ is shown in FIG. 1 as performed in a mixer-settler. As discussed above, alternative separation devices can be used instead of a mixer-settler including where such purification and separation are performed in one step.

The filtration vessel 600 and its contents are cooled, and the purified MTBHQ solidifies. The polar solvent is separated as the filtrate and recycled 610 to the distillation column 200. Finally, the purified MTBHQ is collected 620 from the filtration vessel 600.

Experimental

The following examples are put forth so as to provide those of ordinary skill in the art with a complete disclosure and description of how the methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.) but some errors and deviations should be accounted for.

EXAMPLE 1

An aqueous stream containing 3.5% (wt.) MTBHQ assaying 99.2% (wt.) was passed through a rotating disc column at a flow rate of 18 gallons per hour ("GPH"). A toluene feed was added at a rate of 0.12 GPH. Both feeds were heated to 85° C. The raffinate was found to contain 2.0% (wt.) MTBHQ assaying >99.9% (wt.). A 1 gallon sample of the raffinate was cooled to 15° C. and filtered. The filtered solid was dried and analyzed. The material was found to contain 90 ppm DTBHQ. The resulting material met all Food Chemicals Codex Specifications for TBHQ.

EXAMPLE 2

This example illustrates the purification of crude, water-wet 77.1% (wt.) MTBHQ assaying 98.66% (wt.) MTBHQ and 0.9%(wt.) DTBHQ by the process of the present invention with naphtha as the non-polar solvent. To a 2-liter flask, 150 grams of naphtha, 120 grams of crude, water-wet MTBHQ and 1.2 grams DTBHQ were charged. The flask was inerted and the contents heated to 85° C. over a 20-minute period. The batch was held at 85° C. for 45 minutes. The aqueous layer was separated and cooled to 1 5° C. The MTBHQ was collected by filtration and dried. The assay of the product was 99.71% by gas chromatography, and all TBHQ Food Chemicals Codex Specifications were met. The recovery was 92%.

EXAMPLE 3

The experiment described in Example 2 was carried out with heptane as the nonpolar solvent. The resulting purity and recovery was equivalent to that of Example 2.

EXAMPLE 4

The experiment described in Example 1 was carried out using a horizontal mixer settler. The aqueous feed was held at 24 GPH while the toluene feed was held at 0.75 GPH. The MTBHQ concentration in the aqueous feed was 2.41% (wt.). The raffinate concentration was 2.05% (wt.), representing an 85% recovery. The product isolated by the procedure described in example 1 met all TBHQ Food Chemicals Codex Specifications.

EXAMPLE 5

The experiment described in Example 4 was carried out using a Scheibel column. The parameters were as follows:

aqueous feed concentration 2.25% (wt.) MTBHQ, aqueous feed rate 8 GPH, toluene feed rate 0.16 GPH. The raffinate contained 1.2% (wt.) TBHQ, meeting all Food Chemicals Codex Specifications after isolation.

EXAMPLE 6

This example illustrates the purification of crude, water-wet 77.1% (wt.) MTBHQ assaying 98.66% (wt.) MTBHQ and 0.9% (wt.) DTBHQ by the process of the present invention with toluene as the non-polar solvent. To a 2-liter pressure vessel, 200 g toluene, 600 g water, 390 grams of MTBHQ and 8 grams DTBHQ were charged. The batch was held at 105° C. and 30 psig for 45 minutes. The aqueous layer was separated and cooled to 15° C. The MTBHQ was collected by filtration and dried, meeting Food Chemicals Codex Specifications for TBHQ.

Throughout this application, various publications are referenced. The disclosures of these publications in their entireties are hereby incorporated by reference into this application in order to more fully describe the state of the art to which this invention pertains.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

We claim:

1. A method of making purified monotertiarybutyl hydroquinone comprising less than 0.2% (wt.) of 2,5 ditertiarybutyl hydroquinone, wherein the method comprises:
    (a) heating a first composition in a solvent mixture, wherein the first composition comprises monotertiarybutyl hydroquinone and 2,5 ditertiarybutyl hydroquinone and the solvent mixture comprises a polar solvent and a non-polar solvent to substantially strip-off the non-polar solvent;
    (b) solidifying at least part of the 2,5 ditertiarybutyl hydroquinone;
    (c) separating the solidified 2,5 ditertiarybutyl hydroquinone from the non-solidified first composition to form a second composition comprising the non-solidified first composition and the polar solvent;
    (d) mixing the second composition with a non-polar solvent of the same type as the non-polar solvent of step (a);
    (e) separating the polar solvent from the non-polar solvent, wherein the polar solvent contains the purified monotertiarybutyl hydroquinone; and
    (f) separating the purified monotertiarybutyl hydroquinone from the polar solvent to produce purified monotertiarybutyl hydroquinone comprising less than 0.2% (wt.) of 2,5 ditertiarybutyl hydroquinone.

2. The method of claim 1, wherein the non-polar solvent of step (d) comprises the non-polar solvent stripped-off from the solvent mixture in step (a).

3. The method of claim 1, wherein the separated non-polar solvent and/or polar solvent from step (e) is recycled to form at least part of the solvent mixture in step (a).

4. The method of claim 1, wherein the first composition from step (a) is produced by reacting hydroquinone with either isobutylene or tertiarybutyl alcohol in the presence of a strong acid catalyst.

5. The method of claim 1, wherein the non-polar solvent of steps (a) and (d) comprises toluene, xylene, n-heptane, octane, isooctane, cyclohexane, or naphtha.

6. The method of claim 1, wherein the non-polar solvent of steps (a) and (d) comprises toluene.

7. The method of claim 1, wherein the non-polar solvent of steps (a) and (d) comprises toluene and the polar solvent comprises water.

8. The method of claim 1, wherein the polar solvent comprises water.

9. The method of claim 1, wherein separation of the solidified 2,5 ditertiarybutyl hydroquinone from the second composition in step (c) comprises performing step (c) by filtration and/or centrifugation.

10. The method of claim 1, wherein mixing the second composition with a nonpolar solvent in step (d) comprises performing step (d) in a rotating disc column, Scheibel column, vertically agitated extractor, fixed bed extractor, high pressure extractor, vertical mixer-settler, horizontal mixer-settler, and/or one or more vessel liquid-liquid extractors.

11. The method of claim 1, wherein steps (d) and (e) are substantially performed at a temperature at or above the melting point temperature of the non-solidified first composition present in the second composition.

12. A method of making purified monotertiarybutyl hydroquinone comprising less than 0.2% (wt.) of 2,5 ditertiarybutyl hydroquinone, wherein the method comprises:
    (a) heating a composition in a solvent mixture wherein:
        (i) the composition comprises monotertiarybutyl hydroquinone and 2,5 ditertiarybutyl hydroquinone,
        (ii) the solvent mixture comprises a polar solvent and a non-polar solvent, and
        (iii) the composition and solvent mixture are heated to a temperature at or above the melting point of the composition;
    (b) separating the polar solvent from the solvent mixture at a temperature at or above the melting point of the composition, wherein the polar solvent contains the purified monotertiarybutyl hydroquinone; and
    (c) separating the purified monotertiarybutyl hydroquinone from the polar solvent to produce purified monotertiarybutyl hydroquinone comprised of less than 0.2% (wt.) of 2,5 ditertiarybutyl hydroquinone.

13. The method of claim 12, wherein the composition comprises between 95 and 99 weight percent monotertiarybutyl hydroquinone on a dry basis of the composition.

14. The method of claim 12, wherein the non-polar solvent comprises toluene, xylene, n-heptane, octane, isooctane, cyclohexane, or naphtha.

15. The method of claim 12, wherein the polar solvent comprises water.

16. The method of claim 15, wherein the non-polar solvent comprises toluene.

17. The method of claim 12, wherein the separation of step (b) comprises performing step (b) in a rotating disc column, Scheibel column, vertically agitated extractor, fixed bed extractor, high pressure extractor, vertical mixer-settler, horizontal mixer-settler, and/or one or more vessel liquid-liquid extractors.

18. A method of making purified monotertiarybutyl hydroquinone comprising less than 0.2% (wt.) of 2,5 ditertiarybutyl hydroquinone, wherein the method comprises:
    (a) heating a composition in a solvent mixture wherein the composition comprises monotertiarybutyl hydroquinone and 2,5 ditertiarybutyl hydroquinone, and the solvent mixture comprises a polar solvent and a non-polar solvent, (b) separating the polar solvent from the solvent mixture in a liquid-liquid extraction, wherein the polar solvent contains the purified monotertiarybutyl hydroquinone; and (c) separating the purified monotertiarybutyl hydroquinone from the polar solvent to produce purified monotertiarybutyl hydroquinone comprised of less than 0.2% (wt.) of 2,5 ditertiarybutyl hydroquinone.

19. The method of claim 18, wherein the composition comprises between 95 and 99 weight percent monotertiarybutyl hydroquinone on a dry basis of the composition.

20. The method of claim 18, wherein the non-polar solvent comprises toluene, xylene, n-heptane, octane, isooctane, cyclohexane, or naphtha.

21. The method of claim 18, wherein the non-polar solvent is toluene and the polar solvent is water.

22. The method of claim 18, wherein the separation of step (b) comprises performing step (b) in a rotating disc column, Scheibel column, vertically agitated extractor, fixed bed extractor, high pressure extractor, vertical mixer-settler, horizontal mixer-settler, and/or one or more vessel liquid—liquid extractors.

23. The method of claim 18, wherein in steps (a) and (b), the composition and solvent mixture are substantially kept at or above the melting point temperature of the composition.

* * * * *